(12) United States Patent
Ini et al.

(10) Patent No.: US 7,560,573 B2
(45) Date of Patent: Jul. 14, 2009

(54) PROCESS FOR THE PREPARATION OF (S)-(-)-N,N-DIMETHYL-3-(2-THIENYL)-3-HYDROXYPROPANANINE, A DULOXETINE INTERMEDIATE

(75) Inventors: Santiago Ini, Haifa (IL); Yaron Shmuely, Hedera (IL); Mili Abramov, Givataim (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

(21) Appl. No.: 11/709,560

(22) Filed: Feb. 21, 2007

(65) Prior Publication Data

US 2008/0015363 A1 Jan. 17, 2008

Related U.S. Application Data

(60) Provisional application No. 60/775,593, filed on Feb. 21, 2006, provisional application No. 60/791,103, filed on Apr. 10, 2006, provisional application No. 60/792,812, filed on Apr. 17, 2006.

(51) Int. Cl.
*C07D 333/16* (2006.01)
(52) U.S. Cl. ...................................... 549/65
(58) Field of Classification Search .............. 549/65
See application file for complete search history.

(56) References Cited

U.S. PATENT DOCUMENTS

| 5,023,269 A | 6/1991 | Robertson et al. |
| 5,362,886 A | 11/1994 | Berglund |
| 5,491,243 A | 2/1996 | Berglund |
| 6,541,668 B1 | 4/2003 | Kjell et al. |
| 2006/0063943 A1 | 3/2006 | Sakai et al. |
| 2006/0194869 A1 | 8/2006 | Ini et al. |
| 2007/0167636 A1 | 7/2007 | Butchko et al. |

FOREIGN PATENT DOCUMENTS

| EP | 0 457 559 A2 | 11/1991 |
| EP | 1 506 965 A | 2/2005 |
| JP | 2004 123596 | 4/2004 |
| WO | WO 2004/031168 A | 4/2004 |
| WO | WO 2007/077580 | 7/2007 |
| WO | WO 2007/096707 | 8/2007 |

OTHER PUBLICATIONS

Astleford, B.A. & Weigel, L.O., "Resolution Versus Stereoselective Synthesis in Drug Development: Some Case Studies," in Chirality in Industry II: Developments in the Commercial Manufacture and Applications of Optically Active Compounds, 99-117 (John Wiley & Sons, 1997).
Bopp, R.J. et al., "Practical Considerations for Chiral Separations of Pharmaceutical Compounds," *LG-GC*, 6(6): 514, 516, 518, 520, 522 (Advanstar Comm., Cleveland OH 1988).
Fujima, Yoshito et al., "Synthesis of (S)-3-(N-Methylamino)-1-(2-thienyl)propan-1-ol: Revisiting Eli Lilly's Resolution-Racemization-Recycle Synthesis of Duloxetine for Its Robust Processes," *Organic Process Research & Development*, 10(5): 905-913 (2006).
Sakai, K. et al., "Resolution of 3-(methylamino)-1-(2-thienyl)propan-1-ol, a new key intermediate for duloxetine, with (S)-mandelic acid," *Tetrahedron: Asymmetry*, 14(12): 1631-1636 (2003).
Tao, Xiao et al., "(R)-3-Hydroxy-N, N-dimethyl-3-(2-thienyl)propanamine," *Acta Crystallographica, Section E: Structure Reports Online*, E62(11): 05202-05203 (Nov. 2006).

*Primary Examiner*—Taofiq A Solola
(74) *Attorney, Agent, or Firm*—Kenyon & Kenyon LLP

(57) ABSTRACT

A chiral resolution process for the preparation of (S)-AT-OL, and a process for the racemization of AT-OL are provided.

22 Claims, No Drawings

PROCESS FOR THE PREPARATION OF (S)-(-)-N,N-DIMETHYL-3-(2-THIENYL)-3-HYDROXYPROPANANINE, A DULOXETINE INTERMEDIATE

CROSS REFERENCE TO RELATED APPLICATIONS

The present application claims the benefit of the following U.S. Provisional Patent Application Nos. 60/775,593 filed 21 Feb. 2006, 60/791,103 filed 10 Apr. 2006 and 60/792,812 filed 17 Apr. 2006.

FIELD OF THE INVENTION

The present invention provides processes for preparing a duloxetine intermediate.

BACKGROUND OF THE INVENTION

Duloxetine is a dual reuptake inhibitor of the neurotransmitters serotonin and norepinephrine. It has application for the treatment of stress urinary incontinence (SUI), depression, and pain management. Duloxetine hydrochloride has the following chemical name: (+)-N-methyl-3-(1-naphthalenyloxy)-3-(2-thienyl)propanamine hydrochloric acid salt and the structure:

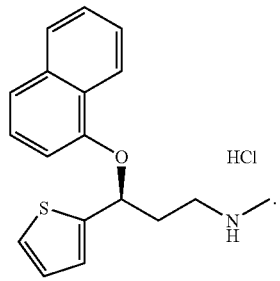

Duloxetine base, as well as processes for its preparation, is disclosed in U.S. Pat. No. 5,023,269 (U.S. '269). EP patent no. 457559, and U.S. Pat. No. 5,491,243 (U.S. '243) and U.S. Pat. No. 6,541,668 provide an improved synthetic route for the preparation of duloxetine base.

The preparation of the enantiomerically pure duloxetine intermediate (S)-AT-OL by its chiral resolution is exemplified in U.S. Pat. No. 5,362,886 (U.S. '886) and in WO 2004/031168, by the use of (S)-(+)-mandelic acid and (−)-2,3:4,6-Di-O-isopropylidene-2-keto-L-gulonic acid, respectively. The U.S. '886 patent describes the preparation of duloxetine by the chiral resolution of N,N-Dimethyl-3-(2-thienyl)-3-hydroxypropanamine (rac-AT-OL) with (S)-mandelic acid (Stage a), its reaction with fluoronaphtalene (Stage b) to give N,N-Dimethyl-3-(1-naphthalenyloxy)-3-(2-thienyl)propanamine (DNT), demethylation with phenyl chloroformate (Stage c), basic hydrolysis in the presence of (Stage d), and acidification (Stage e) in accordance with the following Scheme 1.

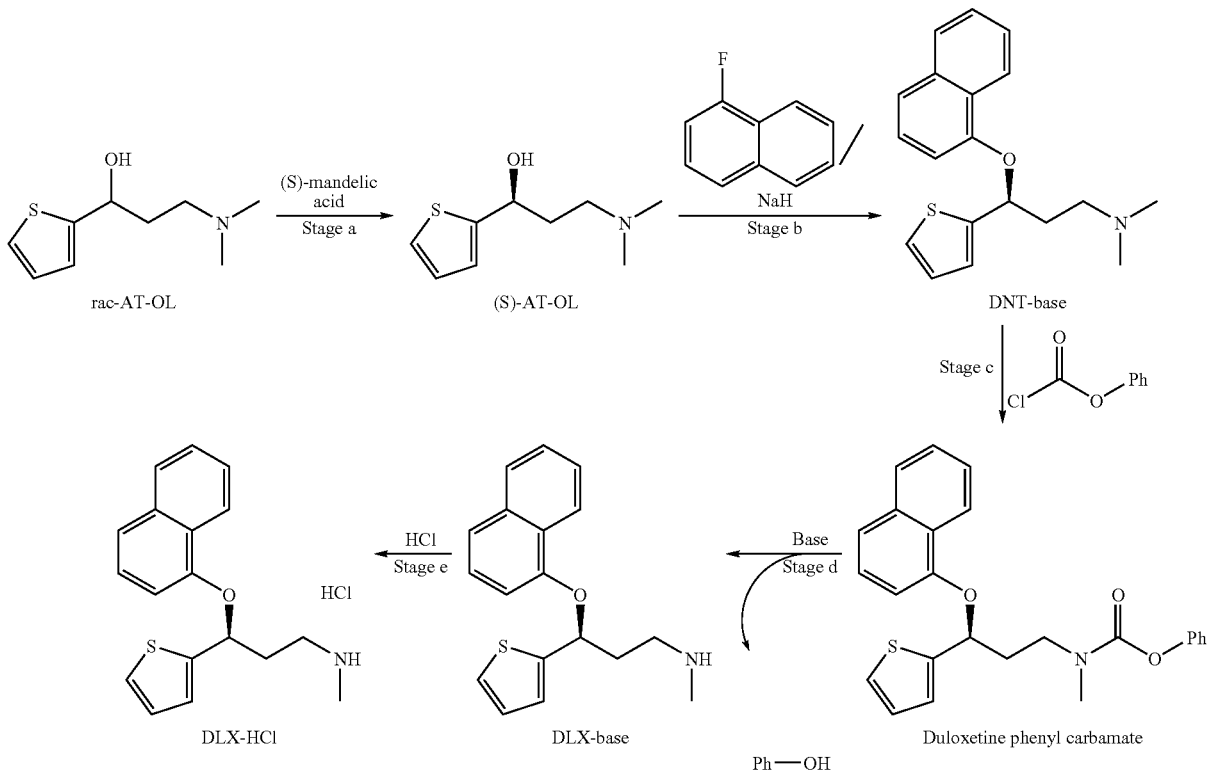

In U.S. Pat. No. 5,362,886, a process for chiral resolution of (S)-AT-OL is disclosed where a reaction mixture is substantially worked-up, and then combined with MTBE (methyl t-butyl ether) and concentrated. The concentrated MTBE containing reaction mixture is then combined with (S)-(+)-mandelic acid in ethanol at 50° C., followed by recovery of the mandelate. The process of this patent does not attempt to recycle the (R)-AT-OL remaining in the mother liquor.

US '269 describes the preparation of enantiomerically pure (S)-AT-OL by its chiral resolution of the racemic N,N-Dimethyl-3-(2-thienyl)-3-hydroxypropanamine (rac-AT-OL) with benzoyl or tartaric acid.

Additionally, the literature proposed a method for racemization of the undesired enantiomer in MTBE (Astleford, B. A.; Weigel, L. O. Resolution Versus Stereoselctive Synthesis in Drug Development: Some Case Studies. In Chirality in Industry II: *Developments in the Comercial Manufacture and Applications of Optically Active Compounds*; Collins, A. N., Sheldrake, G. N., Crosby, J., Eds.; John Willey & Sons: Chichester, 1997; pp 99-117). The process described herein can require substantial work-up, and a change of solvents before the chiral resolution process.

In order to get the maximum yield in the preparation of (S)-AT-OL, there is a need in the art for an improved and efficient synthetic route for the preparation of (S)-AT-OL. The processes of the prior art result in a relatively high amount of (R)-AT-OL. Furthermore, the processes of the art lack a continuous one pot process that efficiently recycles (R)-AT-OL, using the initial solvent system used for the chiral resolution.

SUMMARY OF THE INVENTION

In one embodiment, the present invention provides a one pot continuous process for preparing (S)-AT-OL or (S)-AT-OL mandelate comprising:

a) converting (R)-AT-OL to (R/S)-AT-OL in a mixture of a $C_{1-8}$ alcohols and a $C_{2-8}$ ether in presence of an acid;

b) reacting the (R/S)-AT-OL with (S)-(+)-mandelic acid in the mixture to obtain (S)-AT-OL mandelate; and c) optionally converting the (S)-AT-OL mandelate to (S)-AT-OL.

In one embodiment, the present invention provides a one pot continuous process for preparing (S)-AT-OL or (S)-AT-OL mandelate comprising the steps of:

a) reacting a mixture of (R/S)-AT-OL in a mixture of a $C_{1-8}$ alcohol and a $C_{2-8}$ ether with (S)-(+)-mandelic acid to precipitate (S)-AT-OL mandelate, thereby obtaining a mother liquor enriched in (R)-AT-OL;

b) converting the (R)-AT-OL to (R/S)-AT-OL by combining the mother liquor with an acid;

c) reacting (R/S)-AT-OL with (S)-(+)-mandelic acid to precipitate (S)-AT-OL mandelate; and d) optionally converting the (S)-AT-OL mandelate to (S)-AT-OL.

In one embodiment, the present invention provides a process for the racemization of enantiomerically enriched (R)-AT-OL comprising combining enantiomerically enriched AT-OL, a solvent selected from the group consisting of a $C_{1-8}$ alcohol, water, an aromatic hydrocarbon, a $C_{2-8}$ ester, a $C_{2-8}$ ether and a $C_{3-8}$ ketone and mixtures thereof, and an acid to obtain (R,S)-AT-OL.

In one embodiment, the present invention provides a chiral resolution process for preparing (S)-AT-OL, comprising combining racemic AT-OL with (S)-mandelic acid and a solvent selected from the group consisting of: water, $C_{1-8}$ alcohols, $C_{3-8}$ ketones, $C_{2-8}$ alkyl esters, $C_{5-8}$ aromatic hydrocarbons, and mixtures thereof to obtain a reaction mixture, and recovering the obtained (S)-AT-OL.

Also provided is the tse of the process of any of the preceding claims for preparation of DNT or a salt thereof, or duloxetine or a pharmaceutically acceptable salt of duloxetine.

DETAILED DESCRIPTION OF THE INVENTION

As used herein the term "(S)-AT-OL" refers to: (S)-(−)-N,N-Dimethyl-3-(2-thienyl)-3-hydroxypropanamine.

As used herein the term "(R)-AT-OL" refers to: (R)-(+)-N,N-Dimethyl-3-(2-thienyl)-3-hydroxypropanamine.

As used herein the term "(rac)-AT-OL" refers to: racemic N,N-Dimethyl-3-(2-thienyl)-3-hydroxypropanamine.

The present invention provides an efficient method for the preparation of Duloxetine by improving the process for the preparation of (S)-AT-OL.

The present invention provides racemization and chiral resolution processes which are suitable for industrial scale. These processes result in a low level of the R-enantiomer. Furthermore, it has been discovered that the processes can be carried out in one pot, without removing or changing solvents used in the chiral resolution process when carrying out racemization, or vice versa. In the one pot process, the (R)-AT-OL remaining in the mother liquor can be racemized and reacted with mandelic acid without changing solvents.

The following scheme illustrates the racemization and chiral resolution steps:

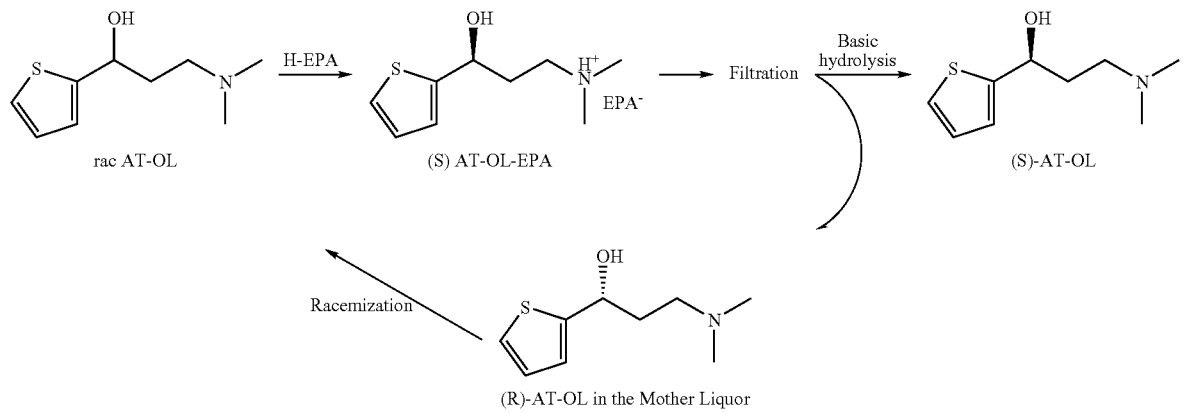

H-EPA: enantiomeric pure acid

In one embodiment, the present invention provides a process for the racemization of enantiomerically pure or enriched AT-OL. The process comprises combining enantiomerically pure AT-OL, an organic solvent selected from the group consisting of: a $C_{1-8}$ alcohol, water, an aromatic hydrocarbon, a $C_{2-8}$ ester, a $C_{2-8}$ ether and a $C_{3-8}$ ketone and mixtures thereof, and an acid to increase ratio of (R)-AT-OL to (S)-AT-OL. The process is preferably carried out until achieving substantially racemic (R,S)-AT-OL Preferred $C_{1-8}$ alcohols are selected from methanol, ethanol, n-propanol, isopropyl alcohol, n-butanol, 2-butanol, isobutanol, and pentanol.

Preferred aromatic hydrocarbons are selected from benzene, toluene, and xylene.

Preferred $C_{2-8}$ esters are selected from ethyl formate, n-propyl formate, i-propyl formate, n-butyl formate, s-butyl formate, i-butyl formate, t-butyl formate, methyl acetate, ethyl acetate, n-propyl acetate, i-propyl acetate, n-butyl acetate, s-butyl acetate, i-butyl acetate, t-butyl acetate, methyl propionate, ethyl propionate, n-propyl propionate, i-propyl propionate, butyl propionate, methyl butyrate, ethyl butyrate, n-propyl butyrate, i-propyl butyrate, butyl butyrates, methyl isobutyrate, ethyl isobutyrate, propyl isobutyrates and butyl isobutyrates.

Preferred $C_{2-8}$ ethers are selected from ethyl ether and methyl t-butyl ether.

Preferred $C_{3-8}$ ketones are selected from acetone and methyl iso-butyl ketone.

Most preferably, the organic solvent is selected from the group consisting of isopropyl alcohol, water, methyl t-butyl ether and ethanol. In one preferred embodiment the solvent is a mixture of methyl t-butyl ether and ethanol.

Preferably, the acid is selected from the group consisting of HCl and $H_2SO_4$.

The obtained racemic (R,S)-AT-OL can be recovered by any method know in the art. Preferably, basic hydrolysis is used to recover the racemic (R,S)-AT-OL.

Typically, the acidic mixture containing the racemic (R,S)-AT-OL is maintained, while stirring, for about 15 minutes to about 48 hours, more preferably for about 22 hours, and is further combined with a base and water.

Preferably, the base is an organic or inorganic base. More preferably, the base is selected from the group consisting of: alkali metal hydroxide, alkali metal alkoxides, and carbonates. Even more preferably, the base is selected from the group consisting of KOH and NaOH. Most preferably, the base is NaOH.

Preferably, the product is extracted in an additional organic solvent. Preferably, the additional organic solvent is a $C_{2-8}$ ester, more preferably, ethyl acetate.

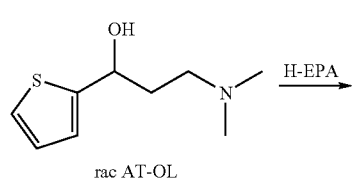

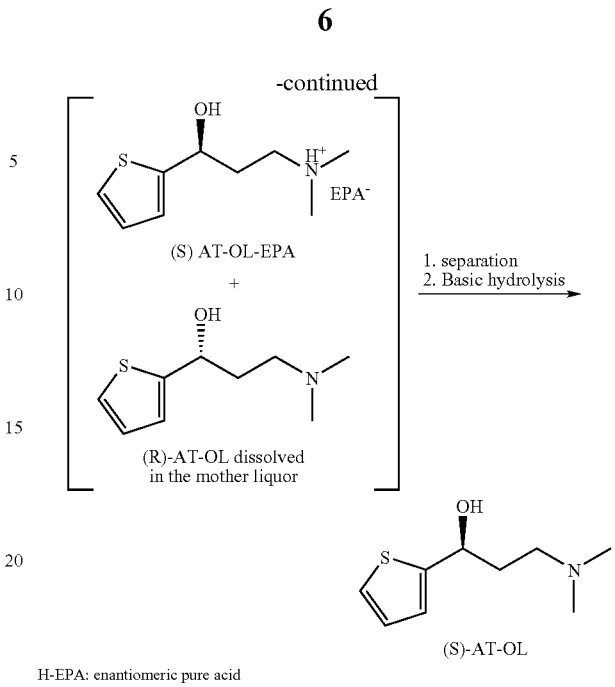

H-EPA: enantiomeric pure acid

According to the process described above, the racemic AT-OL reacts with an enantiomerically pure acid to give a diasteriomerically enriched salt of the enantiomerically pure acid. This salt is filtrated out and separated from the undesired enantiomer (R), and converted to the enantiomerically pure (S)-AT-OL. This conversion can be carried out by reacting the salt with a base in an aqueous reaction mixture. Examples of bases include sodium and potassium hydroxide. Other methods known n the art can also be used for the conversion.

The undesired enantiomer R is racemized and is then subjected to chiral resolution. In one embodiment, the present invention provides a chiral resolution process for preparing (S)-AT-OL, comprising combining racemic AT-OL with (S)-mandelic acid in a solvent selected from the group consisting of: water, $C_{1-8}$ alcohols, $C_{3-8}$ ketones, $C_{2-8}$ alkyl esters, $C_{5-8}$ aromatic hydrocarbons, and mixtures thereof to obtain a reaction mixture, and recovering the obtained (S)-AT-OL.

Preferably, the organic solvent is selected from the group consisting of isopropanol, methyl iso-butyl ketone, and toluene.

The combining can be carried out at a temperature of about room temperature to about reflux. Preferably, racemic AT-OL is combined with (S)-mandelic acid in the solvent at a temperature of about 50° C.

The reaction mixture may be further heated to accelerate the chiral resolution process. Preferably, the heated reaction mixture is maintained after a precipitate appears, more preferably for about 45 minutes.

Preferably, the heated reaction mixture is cooled to a temperature of about 15° C. to about 25° C., to obtain a precipitate. The precipitate is then recovered by any method known in the art, preferably by filtering and drying.

During chiral resolution, the desired enantiomer is separated from the undesired enantiomer, and converted to the enantiomerically pure (S)-AT-OL. Thus, since the enantiomer (R) is lost, the overall yield of the process can not reach more than 50%. To ameliorate this problem, the present invention further provides the recycling of the undesired R enantiomer left after chiral resolution, by the racemization of the R enantiomer, followed by additional chiral resolution.

The (S)-AT-OL prepared according to the above process may be recovered by any method known in the art, such as separating the phases, and concentrating the organic phase until a dry residue is formed. Prior to separation, the (S)-AT-OL may be washed in order to remove inorganic impurities, or organic impurities that are miscible in water.

The present invention also provides a one pot process where a mixture of a $C_{1-8}$ alcohols and a $C_{2-8}$ ether is used. Specifically, in one embodiment, the present invention provides a one pot continuous process wherein the mother liquor having enriched (R)-AT-OL is converted into (R,S)-AT-OL in the same solvent mixture, without removal of an individual component of the solvent (the ratios of the solvents can be different at each step). The mother liquor can be that obtained after a first step of chiral resolution. Preferably the solvent mixture is a mixture of MTBE and ethanol. The one pot process can be repeated several times until the yield obtained in no longer economically desirable.

The one pot process can also start from a source of (R)-AT-OL or a salt thereof other than the mother liquor. For example, (R)-AT-OL can be a residue obtained by evaporating the mother liquor or it can be a salt obtained by reacting an acid with (R)-AT-OL. In this process, (R)-AT-OL is racemized in a mixture of MTBE and ethanol as described above and then subjected to chiral resolution in the same solvent mixture (the ratios of the solvents can be different at each step). Alternatively, the starting material can be a residue of (R,S)-AT-OL or a salt thereof, in which it is subjected to chiral resolution in the same solvent mixture to obtain (R)-AT-OL in the mother liquor, followed by racemization in the mother liquor and an addition chiral resolution.

The (S)-AT-OL prepared in any of the above processes is then converted to DNT. This conversion can be carried out by methods known in the art. DNT can be prepared by reacting (S)-AT-OL with 1-fluoronaphthalene or 1-chloronaphthalene in the presence of a base. In one embodiment, DNT is prepared by providing a solution of a base selected from the group consisting of: alkali metal hydroxide, sodium and alkali metal alkoxides, AT-OL and polar aprotic solvent at a temperature of from about 15° C. to about the reflux temperature of the solvent; combining the solution with 1-fluoronaphthalene or 1-chloronaphthalene, with or without a phase transfer catalyst, to obtain a mixture; heating the mixture to a temperature of from about room temperature to about the reflux temperature of the solvent and recovering DNT.

The DNT prepared according to the above process may be recovered in its base form or as an acid salt, by any method known in the art, such as separating the phases, and concentrating the organic phase until a dry residue is formed. Prior to separation, the DNT may be washed in order to remove inorganic impurities, or organic impurities that are miscible in water.

In another embodiment, the present invention provides processes for converting the obtained DNT to duloxetine, or a pharmaceutically acceptable salt thereof such as duloxetine hydrochloride.

The conversion of DNT to a pharmaceutically acceptable salt of duloxetine may be performed by any method known in the art, such as the one described in U.S. Pat. No. 5,023,269 or in US20060194869 for making duloxetine HCl. Preferably, the conversion is performed by dissolving DNT in an organic solvent, and combining it with an alkyl haloformate. That step will yield duloxetine alkyl carbamate, which can be combined with an organic solvent and a base, to yield duloxetine. The duloxetine may then be converted to a pharmaceutically acceptable salt. More preferably, the conversion is performed by dissolving DNT in a water immiscible organic solvent; adding alkyl chloroformate at a temperature of about 5° C. to less than about 80° C. to obtain duloxetine alkyl carbamate, combining the duloxetine alkyl carbamate with an organic solvent and a base; maintaining the reaction mixture at reflux temperatures for at least 1 to 3 hours; cooling, and adding water and an additional amount of an organic solvent; recovering duloxetine; combining the duloxetine with a solvent; adding hydrochloric acid until a pH of about 3 to about 4 is obtained; maintaining the reaction mixture to obtain a solid residue; and recovering duloxetine HCl.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

HPLC Method for Measuring Enantiomeric Purity:

| | |
|---|---|
| Column: | Daicel Chiralcel OD, 10u, 250 × 4.6 mm |
| Eluent: | 970 mL Hexane; 30 mL Isopropanol; 2 mL Diethylamine |
| Sample volume: | 50 µL |
| Flow: | 1 mL/min. |
| Detector: | 230 nm |
| Column temperature: | 30° C. |
| Sample concentration: | 0.02 mg/mL |

Example 1

Repetition of the Chiral Resolution in Preparation 1 in U.S. Pat. No. 5,362,886 (2× scale)

The chiral resolution of AT-OL in MTBE/ethanol with mandelic acid (Repetition 1 in U.S. Pat. No. 5,362,886) was repeated. A level of 7.01% of enantiomer R was measured.

A solution of 8.2 g of (S)-mandelic acid in 25 ml ethanol (heated at 50° C. for dissolution) was added to a solution of 20 g (R,S)-AT-OL in 300 ml of MTBE at 50° C. The resulting mixture was heated to reflux for 45 minutes, and then cooled to room temperature and stirred for overnight (in the patent stirring is carried out for one hour). The resulting solid was filtered, and dried in a vacuum oven to give 16 g of (S)-AT-OL mandelate (enantiomer R: 7.01%).

Example 2

Chiral Resolution of AT-OL in IPA

A solution of 2 g of (S)-mandelic acid in 10 ml IPA (heated at 50° C. for dissolution) was added to a solution of 5 g (R,S)-AT-OL in 40 ml of IPA at 50° C. The resulting mixture was heated to reflux for 45 minutes, and then cooled to room temperature. The resulting solid was filtered, and dried in a vacuum oven to give 3.5 g of (S)-AT-OL mandelate (enantiomer R: 15.03%).

Example 3

Chiral Resolution of AT-OL in MIBK

A solution of 2 g of (S)-mandelic acid in 10 ml MIBK (heated at 50° C. for dissolution) was added to a solution of 5 g (R,S)-AT-OL in 10 ml of MIBK at 50° C. The resulting mixture was heated to reflux for 45 minutes, and then cooled to room temperature. The resulting solid was filtered, and dried in a vacuum oven to give 3.8 g of (S)-AT-OL mandelate (enantiomer R: 3.87%).

Example 4

Chiral Resolution of AT-OL in Toluene

A solution of 2 g of (S)-mandelic acid in 10 ml toluene (heated at 50° C. for dissolution) was added to a solution of 5 g (R,S)-AT-OL in 10 ml of toluene at 50° C. The resulting mixture was heated to reflux for 45 minutes, and then cooled to room temperature. The resulting solid was filtered, and dried in a vacuum oven to give 2.44 g of (S)-AT-OL mandelate (enantiomer R: 2.97%).

Example 5

Racemization of AT-OL in Isopropyl and HCl

A 150 ml reactor three necked flask equipped with mechanical stirrer, thermometer, and condenser was charged with 2 g of AT-OL (ee: 99.9%) and 20 ml of isopropyl alcohol at room temperature. The mixture was stirred and 5 ml HCl [32%] were added and stirred for an additional time. After 22 hours, 8 ml of sodium hydroxide [22%] were added followed by 20 ml ethyl acetate and 20 ml water.

After phase separation, the water phase was extracted with ethyl acetate, and the organic extracts were combined and concentrated to dryness to give an ee of less than 1%.

Example 6

Racemization of AT-OL in Isopropyl and HCl

A 150 ml reactor three necked flask equipped with mechanical stirrer, thermometer, and condenser was charged with 2 g of AT-OL (ee: 99.9%) and 20 ml isopropyl alcohol at room temperature. The mixture was stirred and 1.2 ml $H_2SO_4$ (98%) were added and stirred for an additional time. After 22 hours, 8 ml of sodium hydroxide (22%) were added followed by 20 ml ethyl acetate and 20 ml water.

After phase separation, the water phase was extracted with ethyl acetate, and the organic extracts were combined and concentrated to dryness to give an ee of less than 1%.

Example 7

Racemization of AT-OL in MTBE/EtOH and HCl

A 100 ml three necked flask equipped with mechanical stirrer, thermometer, and condenser was charged with 5 g of AT-OL (ee: 99.99%) and 40 ml of MTBE and 10 ml ethanol and stirred at room temperature. To the mixture were added 12 ml of HCl [32%] and stirred for an additional time. After 22 hours, 20 ml of sodium hydroxide (22%) were added followed by 40 ml ethyl.

After phase separation, the water phase was extracted with 40 ml ethyl acetate, and the organic extracts were combined and concentrated to dryness to give an ee of less than 1%.

Example 8

Racemization of AT-OL in Water and HCl

A 150 ml three necked flask equipped with mechanical stirrer, thermometer, and condenser was charged with 5 g of AT-OL (ee: 99.9%) and 50 ml of water and stirred at room temperature. To the mixture were added 12 ml HCl (32%) and stirred for an additional time. After 22 hours, 20 ml of sodium hydroxide (22%) were added followed by 40 ml ethyl acetate.

After phase separation, the water phase was extracted with 40 ml ethyl acetate, and the organic extracts were combined and concentrated to dryness to give an ee of less than 1%.

Example 9

One Pot Reaction for the Preparation of (S)-AT-OL and Racemization of the Undesired Enantiomer Preparation of AT-OL-Mandelate A solution of 90 g of AT-ONE, in 290 ml methanol and 145 ml of water was cooled to 0° C. and 14 ml of NaOH [47%] were gradually added till pH 10. To the resulting solution was added portion added 12.1 g of sodium borohydride and the mixture was allowed to warm to room temperature overnight. The methanol was evaporated under reduced pressure and 250 ml were added followed by the slowly addition of concentrated HCl till pH 1.5 and stirred for an additional 20 minutes. After basification with NaOH the phases were separated, the water phase was washed with MTBE and the combined organic phases were washed with brine. To the MTBE solution was added a solution of 16.4 g of (S)-mandelic acid in 40 ml ethanol and the resulting mixture was stirred at reflux for 1.25 hours and then cooled to room temperature. The resulting solid was filtered from the mother liquor, washed with MTBE and dried in a vacuum oven to give 25 g of (S)-AT-OL mandelate.

Racemization of (R)-AT-OL-Prophetic

The mother liquor from the above example is stirred at room temperature. HCl [32%] is added to the mother liquor and stirred for an additional time. After 22 hours, sodium hydroxide (22%) is added followed by ethyl acetate. After phase separation, the water phase is extracted with ethyl acetate, and the organic extracts are combined and concentrated to dryness to give an ee of less than 1%.

Preparation of (S)-AT-OL, by Hydrolysis of (S)-AT-OL Mandelate

To 20 g of AT-OL-mandelate (obtained previously) in a mixture of 60 ml water and 90 ml MTBE were added NaOH [47%] till pH 9 and stirred at room temperature. After 30 minutes the phases were separated, the organic phases were washed with water and the residue evaporated to dryness to give (S)-AT-OL.

What is claimed is:

1. A one pot continuous process for preparing (S)-AT-OL or (S)-AT-OL mandelate comprising:
   a) converting (R)-AT-OL to (R/S)-AT-OL in a solvent mixture of a $C_{1-8}$ alcohol and a $C_{2-8}$ ether in presence of an acid;
   b) reacting the (R/S)-AT-OL with (S)-(+)-mandelic acid in the mixture to obtain (S)-AT-OL mandelate and to obtain a mother liquor enriched in (R)-AT-OL; and
   c) optionally converting the (S)-AT-OL mandelate to (S)-AT-OL.

2. The process of claim 1, wherein the solvent mixture is a mixture of methyl t-butyl ether and ethanol.

3. The process of claim 1, wherein the (R)-AT-OL in the mother liquor obtained after removal of (S)-AT-OL through reaction with (S)-(+)-mandelic acid of step b) is used as the mixture of step a).

4. The process of claim 1, further comprising repeating steps (a) and (b).

5. The process of claim 1, wherein ratio of the ether to the alcohol is different in steps (a) and (b).

6. The process of claim 1, wherein the acid is selected from the group consisting of HCl and $H_2SO_4$.

7. The process of claim 1, wherein after combining with an acid, the mixture is maintained and then combined with a base and water.

8. The process of claim 7, wherein the base is selected from the group consisting of: alkali metal hydroxide, alkali metal alkoxides, and carbonates.

9. The process of claim 8, wherein the base is selected from the group consisting of KOH and NaOH.

10. The process of claim 1, wherein conversion of (S)-AT-OL mandelate to (S)-AT-OL is carried out by reacting the mandelate with a base.

11. The process of claim 10, wherein the base is selected from the group consisting of: alkali metal hydroxide, alkali metal alkoxides, and carbonates.

12. The process of claim 10, wherein the base is selected from the group consisting of KOH and NaOH.

13. A one pot continuous process for preparing (S)-AT-OL or (S)-AT-OL mandelate comprising the steps of:
   a) reacting a mixture of (R/S)-AT-OL in a solvent mixture of a $C_{1-8}$ alcohol and a $C_{2-8}$ ether with (S)-(+)-mandelic acid to precipitate (S)-AT-OL mandelate, thereby obtaining a first mother liquor enriched in (R)-AT-OL;
   b) converting the (R)-AT-OL to (R/S)-AT-OL by combining the first mother liquor with an acid;
   c) reacting (R/S)-AT-OL with (S)-(+)-mandelic acid to precipitate (S)-AT-OL mandelate and to obtain a second mother liquor enriched in (R)-AT-OL; and
   d) optionally converting the (S)-AT-OL mandelate to (S)-AT-OL.

14. The process of claim 13, wherein the solvent mixture is a mixture of methyl t-butyl ether and ethanol.

15. The process of claim 13, wherein the (R)-AT-OL in the second mother liquor obtained after removal of (S)-AT-OL with mandelic acid of step c) is used as the mother liquor of step b).

16. The process of claim 13, further comprising repeating steps (a) and (b).

17. The process of claim 13, wherein the ratio of the ether to the alcohol is different in step(a) and (b).

18. The process of claim 13, wherein after combining with the acid, the mixture is maintained and then combined with a base and water.

19. The process of claim 18, wherein the base is selected from the group consisting of: alkali metal hydroxide, alkali metal alkoxides, and carbonates.

20. The process of claim 13, wherein the acid is selected from the group consisting of HCl and $H_2SO_4$.

21. The process of claim 13, wherein conversion of (S)-AT-OL mandelate to (S)-AT-OL is carried out by reacting the mandelate with a base.

22. The process of claim 21, wherein the base is selected from the group consisting of KOH and NaOH.

* * * * *